United States Patent
Nikitin et al.

(10) Patent No.: US 7,732,220 B2
(45) Date of Patent: *Jun. 8, 2010

(54) METHOD OF ANALYSIS OF A MIXTURE OF BIOLOGICAL AND/OR CHEMICAL COMPONENTS WITH THE USE MAGNETIC PARTICLES AND APPARATUS FOR ITS EMBODIMENT

(75) Inventors: Petr Ivanovich Nikitin, Moscow (RU); Petr Mikhailovich Vetoshko, Moscow (RU)

(73) Assignee: Magnisense Technology Limited, Limassol (CY)

( * ) Notice: Subject to any disclaimer, the term of this patent is extended or adjusted under 35 U.S.C. 154(b) by 0 days.

This patent is subject to a terminal disclaimer.

(21) Appl. No.: 12/078,953

(22) Filed: Apr. 8, 2008

(65) Prior Publication Data

US 2008/0261329 A1    Oct. 23, 2008

Related U.S. Application Data

(63) Continuation of application No. 10/221,107, filed as application No. PCT/RU01/00100 on Mar. 7, 2001.

(30) Foreign Application Priority Data

Mar. 9, 2000    (RU) .............................. 2000105511

(51) Int. Cl.
*G01N 33/553*    (2006.01)
*G01N 27/72*    (2006.01)

(52) U.S. Cl. ..................... 436/526; 324/239; 324/201; 324/204; 324/255

(58) Field of Classification Search ............... 436/526; 324/239, 201, 204, 255
See application file for complete search history.

(56) References Cited

U.S. PATENT DOCUMENTS

| 4,247,406 | A | 1/1981 | Widder et al. |
| 5,656,429 | A | 8/1997 | Adelman |
| 5,916,539 | A | 6/1999 | Pilgrimm |

(Continued)

FOREIGN PATENT DOCUMENTS

JP    2000-56032 A    2/2000

(Continued)

OTHER PUBLICATIONS

International Search Report mailed Dec. 11, 2001 issued in PCT/RU01/00100.

(Continued)

*Primary Examiner*—Mark L Shibuya
*Assistant Examiner*—Pensee T Do
(74) *Attorney, Agent, or Firm*—Jeffrey B. Arnold; Adorno & Yoss LLC (57) ABSTRACT

Disclosed is a method of analysis of a mixture of biological and/or chemical components that entails spatially arranging a chosen component attached to magnetic particles, exposing the particles to a magnetic field, and recording a magnetic induction signal, from which the content of the analyte in the mixture is judged; this includes grouping the chosen component in a probe volume, making the magnetic field alternating, pre-setting its spectrum, at least, at two frequencies, and recording the signal at a frequency, which is a linear combination of these frequencies, during the exposure of the magnetic particles to the field.

11 Claims, 4 Drawing Sheets

U.S. PATENT DOCUMENTS

| | | | |
|---|---|---|---|
| 5,928,958 | A | 7/1999 | Pilgrimm |
| 5,945,525 | A | 8/1999 | Uematsu et al. |
| 6,133,047 | A | 10/2000 | Elaissari et al. |
| 6,437,563 | B1 | 8/2002 | Simmonds et al. |
| 6,548,311 | B1 | 4/2003 | Knoll |

FOREIGN PATENT DOCUMENTS

| | | |
|---|---|---|
| WO | 91/17428 A1 | 11/1991 |
| WO | 97/45740 A1 | 12/1997 |
| WO | 99/27367 A1 | 6/1999 |

OTHER PUBLICATIONS

Examination Report issued in PCT/RU01/00100.

Kriz et al., Magnetic Permeability Measurements in Bioanalysis and Biosensors, Anal. Chem., vol. 68, No. 11, 1996, pp. 1966-1970.

Lalatonne, Y., et al., Charactedrization of magnetic labels for bioassays, Journal of Magnetism and Magnetic Materials, 321 (2009) 1653-1657, Elsevier B.V.

Lenglet, Multiparametric magnetic immunoassays utilizing non-linear signatures of magnetic labels, 321 (2009) 1639-1643, Elsevier B.V.

Nikitin, M.P., et al., Highly sensitive room-temperature method of non-invasive in vivo detection of magnetic nanoparticles, 321 (2009) 1658-1661, Elsevier B.V.

Nikitin, M.P,, et al., Quantitative real-time in vivo detection of magnetic nanoparticles by their nonlinear magnetization, Journal of Applied Physics 103, 07A304 (2008).

Nikitin, P.I., et al., Magnetic Immunoassays, Sensor Letters, vol. 5, 296-299, 2007, American Scientific Publishers.

FIG. 13

METHOD OF ANALYSIS OF A MIXTURE OF BIOLOGICAL AND/OR CHEMICAL COMPONENTS WITH THE USE MAGNETIC PARTICLES AND APPARATUS FOR ITS EMBODIMENT This is a Continuation of copending application Ser. No. 10/221,107, filed Sep. 9, 2002, which is a PCT National Stage of PCT/RU01/00100 filed Mar. 7, 2001, which claims priority to Russian Patent Application No. 2000105511 filed Mar. 9, 2000.

TECHNICAL FIELD

The proposed method refers to the field of development and improvement of means for biochemical analyses and to the field of chemical and bio-sensors.

BACKGROUND ART

A method of biochemical analysis of a mixture of components with the use of magnetic particles is known [Ch. B. Kriz, K. Radevik, D. Kriz, Magnetic Permeability Measurements in Bioanalysis and Biosensors/Anal. Chem. 68, 1996, pp. 1966-1970], which includes the following:

making use of a chosen component attached to magnetic particles;

exposing said magnetic particles to a magnetic field, recording a signal due to the magnetic induction produced by said magnetic particles as a result of their exposure to the magnetic field, judging the content of the analyte in the mixture being analysed from the value of said signal.

According to this method, one introduces particles into a specimen of the mixture to be analysed, which particles carry recognising elements that selectively bind the analyte. Besides, in the mixture being analysed there should be a chosen component attached to magnetic particles. This component binds selectively to the analyte after binding of the latter to the recognising elements, or competes with the analyte for binding to the recognising elements. In exceptional cases when the analyte contains magnetic particles, the chosen component can be the analyte itself.

As this takes place, this method necessarily includes removing from the specimen such magnetic particles that have appeared to be unbound to the carrier particles after the course of the reactions mentioned above. To do so, the specimen is subjected to sedimentation, spinning, and rinsing with a binding buffer solution. Then a certain dose of the specimen is placed in a test-tube, which is inserted in an inductance coil. From the change of the magnetic induction of the coil after inserting the specimen into it the content of the analyte in the medium being analysed is judged.

The drawback of this analogue consists in its high complexity and low throughput because of a large number of operations. This leads also to high cost, insufficient reliability and low accuracy of the results obtained.

The closest to the proposed method is an analogue-method of polynucleotide and protein analysis using magnetisable moieties [U.S. Pat. No. 5,656,429 of Dec. 8, 1997, Polynucleotide and protein analysis method using magnetizable moieties, Int. Cl.: C12 Q 1/68, U.S. Cl.: 435/6,], which comprises the following operations:

choosing a component for attaching magnetic particles to it or a component that is already attached to magnetic particles, this chosen component being either the analyte or another component that allows judging the content of the analyte in the mixture being analysed, spatially arranging said chosen component, attaching magnetic particles to said chosen component or using said chosen component that is already attached to magnetic particles, exposing said magnetic particles to a magnetic field, recording a signal due to the magnetic induction produced by said magnetic particles as a result of their exposure to the magnetic field, judging the content of the analyte in the mixture being analysed from the value of said signal.

In doing so, one distributes components in a prescribed manner (e.g., by electrophoresis) on the surface of a substrate according to the molecular size and the quantity of the components in the mixture being analysed. Magnetic particles are attached to one or another component of the mixture before or after distributing the components on the substrate surface. Then one records the resulting distribution by magnetic reading from the substrate surface similarly to that one reads information from a magnetic disk. From said distribution one obtains information on the content of one or another component in the mixture being analysed. To enable the magnetic reading, the particles are magnetised by a dc magnetic field before or after distributing them on the substrate surface. The magnetic reading itself consists in the measurement of the magnetic induction resulting from the residual magnetisation of the particles. An important merit of the analogue-method is the spatial arranging of magnetic particles that are bound with the analyte or the chosen component. This arranging takes place on the substrate surface in a close proximity to a magnetic reader. Consequently, the reliability of the results is increased, the dimensions of the required apparatus are minimised, and compatibility of the apparatus with microelectronics technologies is ensured.

The drawbacks of this analogue-method are low sensitivity of the method and low accuracy of the results it yields, due to a number of reasons. These are: first, small concentration of the magnetic particles being recorded, which are "spread" on the substrate surface; second, very small residual magnetisation of known particles of micron and submicron size; and, third, well-known negative features of dc measurements. The mentioned reasons result in narrow application area of this method.

An analogue-apparatus for reading results is known for the method of biochemical analysis of a mixture of substances, using magnetic labels [Ch. B. Kriz, K. Radevik, D. Kriz, Magnetic Permeability Measurements in Bioanalysis and Biosensors/Anal. Chem. 68, 1996, pp. 1966-1970], which comprises:

magnetic particles attached to a chosen component of the mixture being analysed, directly or through an intermediate material;

a magnetic field generator, within which action said magnetic particles are situated;

a meter of the magnetic induction produced by said magnetic particles;

an output signal receiver;

a block generating the result, which input is connected to the output of the output signal receiver.

In this apparatus the magnetic induction meter, which is made as an inductance coil, is inserted in one arm of a bridge circuit, which input is connected to the output of the magnetic field generator and the input of the circuit is connected to the input of the output signal receiver.

The operation of this analogue-apparatus relies upon that the presence of magnetic particles in the sample being analysed and situated inside the inductance coil, which serves as the magnetic induction meter, leads to a change in this inductance and, hence, to a misbalance of the bridge circuit. This causes the generation of the output signal of the discussed apparatus.

The drawbacks of this analogue-apparatus are its high complexity and low throughput because the bridge should be precisely balanced for each new measurement. This also leads to high cost and, taking into account environmental temperature instabilities (especially in portable variants of the apparatus), to low accuracy of the results obtained.

The closest to the proposed apparatus is analogue-apparatus used for information reading in the polynucleotide and protein analysis method using magnetisable moieties [U.S. Pat. No. 5,656,429 of Dec. 8, 1997, Polynucleotide and protein analysis method using magnetizable moieties, Int. Cl.: C12 Q 1/68, U.S. Cl.: 435/6], which comprises:

a chosen component of the mixture being analysed, said component being spatially arranged in a prescribed manner;

magnetic particles attached to the chosen component of the mixture being analysed directly or through an intermediate material;

a magnetic field generator, within which action said magnetic particles are situated;

a meter of the magnetic induction produced by said magnetic particles;

an output signal receiver;

a block generating the result, which input is connected to the output of the output signal receiver.

Besides, the components of the mixture being analysed are distributed on the surface of a substrate according to their molecular size, the magnetic field generator and the magnetic induction meter enable generation and, respectively, recording of a signal constant in time.

The operation of the analogue-apparatus relies upon that the magnetic particles attached to one or several chosen components of the mixture being analysed, and distributed along the substrate surface, acquire a residual magnetisation resulting from their exposure to a dc magnetic field. Then by means of a dc magnetic field meter, e.g., a Hall sensor, one records the distribution of the magnetic induction caused by the residual magnetisation on the substrate surface. From this distribution one determines the amount of magnetic particles attached to one or another component of the mixture being analysed, and the content of this component in the mixture.

The drawbacks of this analogue are limited sensitivity of the apparatus and low accuracy of the results obtained. These are due to known negative features of dc measurements, low value of residual magnetisation, and low concentration of magnetic particles, which are spread on the surface of a substrate. The application area of this apparatus is rather narrow, too.

To conclude, the wanted technical result consists in rising signal-to-noise ratio and, hence, increasing measurement accuracy, enhancing sensitivity of the method and apparatus, improving reliability of the data obtained, along with lowering the costs of experiments owing to reduction of the operation number and time needed, amount and dimensions of the apparatus, and, besides, in developing mobile, cheap, high-throughput laboratories for mass tests, in improving the operational flexibility of the method and apparatus and extending their application area.

DISCLOSURE OF INVENTION

To achieve the mentioned technical result, there is proposed a method of analysis of a mixture of biological and/or chemical components with the use of magnetic particles, which comprises:

choosing a component for attaching magnetic particles to it or a component that is already attached to magnetic particles, this chosen component being either the analyte or another component that allows judging the content of the analyte in the mixture being analysed, spatially arranging said chosen component, attaching magnetic particles to said chosen component or using said chosen component that is already attached to magnetic particles, exposing said magnetic particles to a magnetic field, recording a signal due to the magnetic induction produced by said magnetic particles as a result of their exposure to the magnetic field, judging the content of the analyte in the mixture being analysed from the value of said signal, similarly to the analogue-method.

The proposed method differs in that:

spatially arranging said chosen component includes grouping this component in a probe volume;

said magnetic field is alternating, and its spectrum is preset with spectral components, at least, at two frequencies;

said signal is being recorded at such a frequency that is a linear combination of the frequencies of said spectral components, during the exposure of said magnetic particles to said magnetic field.

Besides, said linear combination of the frequencies of said spectral components is the sum or the difference of these frequencies.

Besides, the amplitude of, at least, one of said spectral components is chosen high enough to ensure a non-linear dependence of said magnetic induction on the strength of said magnetic field.

Besides, the amplitudes $A_h$ and $A_l$ of said spectral components, which pertain to the higher and the lower frequencies, respectively, are chosen according to the relationship $A_l/A_h>2$.

Besides, the magnetic field strength vectors pertaining to, at least, two said spectral components, are oriented non-collinear to each other.

Besides, the magnetic particles are made of a soft magnetic material.

Besides, in said probe volume a working surface is formed, and said chosen component is being spatially arranged through binding this component to the working surface.

Besides, the working surface is formed through filling the probe volume with micro-granules.

Besides, said micro-granules are made of polyethylene.

Besides, said micro-granules are made under low pressure from polyethylene stabilised with gamma-radiation.

Besides, the working surface is formed through filling the probe volume with a capillary-porous structure.

Besides, the working surface is formed with immobilising a reagent on it, which is capable of binding the analyte in a selective manner, and through this reagent said chosen component is being bound to the working surface.

Besides, said probe volume is formed from several spatially separated regions, and the possibility to record said signal is ensured for each of said regions.

Besides, in said regions a working surface is formed and on this working surface various reagents are immobilised, which are capable of binding various analytes selectively and through which chosen components are being bound to the working surface, from recording said signal for each of several said regions the information on the contents of several analytes in the mixture being analysed is being obtained.

One of the distinctive features of the proposed method consists in that the spatial arranging of the chosen component of the mixture being analysed with magnetic particles attached to it is accompanied by the grouping of this component in a probe volume. This leads to a substantial increase of the concentration of the magnetic particles being recorded in the region of their exposure to the magnetic field and in close proximity to the magnetic induction meter. This, in turn, results in a drastic increase of the signal being measured against the noise level. The grouping in the probe volume can be done using several approaches. Among them, there are biological or chemical binding as well as adsorption or absorption of particles or molecules of the chosen component in a pre-set spatial region or a number of such regions. Besides, said grouping can be performed through exposure to an inhomogeneous magnetic field, filtration, sedimentation, etc. In a number of cases the grouping can take place near a surface, which is already present in the control volume, or near an intentionally formed working surface. The variants of forming the working surface particularly include chemical modification of a surface present in the control volume, immobilisation of one or another reagent on such a surface, and, besides, the synthesis of a biomolecular matrix or a spacer layer to realise such immobilisation in a two- or three-dimensional region. Among the cases of said grouping, which are the most important in practice, are reactions of selective binding (recognition) of the chosen component and a reagent complementary to it, which is immobilised in the probe volume, in particular, on the formed working surface. The examples of such reactions are various ligand-receptor interactions, antigen-antibody and biotin-avidin binding, etc., as well as binding of complementary DNA fragments (DNA hybridisation). Of good promise for practical applications is to carry out said grouping through selective binding on the large effective working surface of a capillary or porous structure formed in a probe volume similar to a chromatography column or on the working surface of wells of standard microtiter plates (e.g., arrays of 8×12, 16×24, 32×48 wells), which are used in Enzyme-Linked Immuno-Sorbent Assays (ELISA) and other biochemical analyses with biochips.

In doing this, various approaches can be used to employ recognition reactions for arranging the chosen component spatially and obtaining information on the analyte. Besides, there can be different relationships between the analyte and the chosen component. The chosen component can be either the analyte itself or another component, which content in the probe volume enable one to judge directly or indirectly the content of the analyte in the mixture being analysed.

In the simplest case the analyte itself possesses magnetic properties and contains magnetic particles (e.g., ferritin protein). The analyte in this case serves simultaneously as the chosen component, which is being spatially arranged through selective binding with a recognising reagent (e.g., an antibody specific to this protein). In other cases magnetic particles are being attached to the chosen component. Magnetic particles are considered to mean particles that reveal magnetisation under exposure to an external magnetic field and, as a rule, are joined to a material (conjugate) that ensures their biological compatibility.

In another method ("sandwich assay"), the analyte also serves as the chosen component, and magnetic particles are attached to this component in a selective manner, as a rule, before or after selective binding of this component with a recognising reagent. The attachment of the magnetic particles can be done, as the case requires, directly or through an intermediate material. In, particular, it is the intermediate material previously joined to the magnetic particles that is advisable to use to ensure the selectivity of the attachment of the magnetic particles to the analyte. For example, one epitope of the analyte binds selectively to a recognising material while another epitope does to said intermediate material.

In a third method such a chosen component is used that, along with the analyte, is capable of selective binding with a recognising reagent. In this case the chosen component competes with the analyte for binding to the recognising reagent ("competitive assay"). Magnetic particles are being selectively attached to the chosen component, as a rule, before or after its selective binding to the recognising reagent (in a similar manner, directly or through an intermediate material). Otherwise, a chosen component that is already attached to magnetic particles is used. In order to judge the quantity of the analyte in the mixture being analysed from the extent, to which the chosen competitive component binds to the recognising reagent, the mixture must contain a known quantity of the chosen component prior to the analysis. Practically, a known quantity of such a chosen component is usually introduced into the mixture being analysed before the analysis.

In all mentioned modifications of the proposed method there exists a unambiguous relationship between the quantity of the magnetic particles grouped in a specified probe volume due to selective binding of a chosen component, and the sought-for content of the analyte in the mixture being analysed. One records a signal related to the magnetic induction produced by the particles as a result of their exposure to a magnetic field and then judges the quantity of the grouped magnetic particles and the content of the analyte in the mixture.

From the foregoing it is seen that in the proposed method magnetic particles play the role of labels (markers) of a chosen component, similarly to how enzyme, fluorescent, radioactive, and other labels are used in conventional procedures of biochemical analyses.

In doing so, however, one uses an alternating magnetic field and pre-sets its spectrum with spectral components, at least, at two frequencies, and records said signal at such frequency that is a linear combination of the frequencies of said spectral components, during the exposure of said magnetic particles to said magnetic field. The frequency spectrum of the magnetic field acting on the magnetic particles is pre-set with due regard to the properties of the medium to be analysed or a buffer medium, in particular, to specific bands or spectral regions of absorption of high-frequency electromagnetic field by such a medium. For example, when analysing biological solutions it is important to take into account the conductivity and the absorption of water in MHz and GHz ranges.

Measuring the signal during the exposure to the magnetic field is another important distinction from the analogue-method. It enables one to avoid relying on a residual magnetisation. One measures a signal at a combinatorial frequency. Hence one records a parameter related exclusively to the quantity of magnetic particles being detected rather than to the acting magnetic field or magnetic field-induced circuitry interference at the frequency of the field or multiples of it. In general, such a combinatorial frequency is a linear combination of frequencies $f_1$ and $f_2$ as $f_i = m\,f_1 + n\,f_2$, where m and n are positive or negative integers other than zero, and $f_1$ and $f_2$ are, respectively, the greater and the lesser frequency of two said spectral components of the acting magnetic field. In principle, said linear combination may also include a greater number of frequencies of spectral components of the magnetic field. Besides, the values of m and n may vary, as the situation requires. For example, said linear combination may appear as $f_i=f_1 \pm f_2$ (that is, be a sum or a difference of the frequencies of said spectral components), $f_i=f_1 \pm 2\ f_2$, and so on.

It should be noted that, other conditions being equal, one can detect the chosen component with magnetic particles attached to it from measurements of not only at a combinatorial frequency, but also at a frequency multiple to the frequency of the acting magnetic field (i.e., at m=0 or n=0, or under exposure to a magnetic field of one frequency only). In the latter case, the magnetic induction signal measured at a multiple (i.e. double) frequency is also determined by the quantity of the magnetic particles being detected rather than by the amplitude of the acting field, since it is the material of the magnetic particles that introduces a non-linear dependence of the magnetic induction being measured on the strength of the acting magnetic field. It is this non-linear dependence that results in combinatorial and multiple frequencies in the spectrum of the magnetic induction signal. In the proposed method recording a signal at a combinatorial frequency is made use of as a preferred way to distinguish the informational signal from noise and circuit interference.

One may also use various relationships between the amplitudes of said frequency components of the magnetic field. The amplitude of, at least, one of said spectral components is chosen high enough to ensure non-linear dependence of said magnetic induction on the strength of said magnetic field, because this is necessary for combinatorial frequencies to appear. The quantitative measure of the non-linearity used depends on the parameters of the employed circuit, which records the signal at a combinatorial frequency, and on the ability of this circuit to distinguish this signal from noisy background. Lowering the amplitude of the higher frequency component of the acting field spectrum is advisable for realisation of linear regime of measurements of the signal formed, for simplicity of apparatus embodiments, and for lowering the energy consumption. That is why the amplitudes $A_h$ and $A_l$ of said spectral components, which pertain to the higher and the lower frequencies, respectively, are chosen according to the relationship $A_l/A_h>2$.

Thus, in actual practice, it is the lower frequency component of the acting magnetic field that usually provides the non-linear dependence of the magnetic induction produced by said magnetic particles on the strength of the field. To enhance the signal at a combinatorial frequency, the amplitude of said lower frequency component should correspond to the saturation of this dependence or, at least, to the regime close to saturation. This, of course, implies essential non-linearity. For the sake of simplicity one may say that the lower frequency component of the field periodically "switches" the mentioned non-linearity on and off. From experimental realisation of the proposed method it has been found that the amplitude of the lower frequency component can be optimised using various optimisation criteria. For example, the maximum signal at a combinatorial frequency has been obtained at such a value of the lower frequency component amplitude, that the saturation state takes place approximately for half time. To increase stability against external factors (temperature, electromagnetic interference, drifts, etc.), this amplitude is reasonable to choose somewhat higher.

Besides, the magnetic strength vectors pertaining to, at least, two said spectral components, in a number of cases are oriented non-collinear to each other. This is thought to be useful for rising the efficiency of the non-linear interaction between external signals and the system of magnetic particles, for example, when recording a spin echo signal.

The magnetic particles are made of a soft magnetic material in order to increase the magnetic induction, which is the response of the magnetic material of the particles and on which directly the magnitude of the measured signal depends. Besides, commercially available magnetic particles ("magnetic beads"), which are conventionally applied for bio-magnetic separation, can also be used. Usually these are supplied as colloidal mixtures ("ferrofluids"). Such particles are, as a rule, from tens nanometres to tens microns in size, contain a magnetic material (usually $\square Fe_2O_3$, $Fe_3O_4$) in a polymeric entrapment, and are superparamagnetic. The latter term means that the particles reveal magnetic properties only when placed in an external magnetic field but do not reveal residual magnetisation after being removed from this field.

To build up the most favourable conditions for grouping the chosen component in a probe volume and for localising this component in close proximity to the magnetic induction meter, in said probe volume a working surface is purpose formed, and said chosen component is being spatially arranged through binding this component to the working surface. Preferable is the formation of a well-developed working surface with a high effective surface value in a three-dimensional region of the probe volume or the synthesis of a three-dimensional binding biomolecular matrix (i.e., dextrane, peptide spacers, etc.) on one of the surfaces within the probe volume. This provides for a large number of elementary events of selective binding (recognition) of an analyte or a chosen component per unit volume near the magnetic induction meter. As a result, large number of magnetic particles localised near the magnetic induction meter and high level of information signal against noises are ensured. The formation of the working surface may also include physical or chemical treatment or modification of a surface (e.g., etching to provide for binding of one or another reagent or to create a porous structure), immobilisation of bio-reagents, etc., as already mentioned above.

One of the variants of the working surface formation in a probe volume consists in that the probe volume is filled with micro-granules fully or partially. This allows increasing the surface, on which the biochemical reactions of interest occur. This, in turn, leads to the increase of the concentration and the total number of the magnetic particles being grouped and, consequently, of the signal being measured.

Besides, said micro-granules are produced under low pressure from polyethylene stabilised with gamma-radiation. This provides for high immunity of the working surface to chemical and mechanical destructive factors.

Another variant of working surface formation consists in filling the probe volume with a capillary-porous structure fully or partially. Capillary or porous structure can be created in the probe volume through placing capillary or porous materials in it, or by other physical or chemical methods (e.g., etching, annealing, etc.). One of the preferred variants of the proposed method consists in passing the mixture being analysed through a micro-column filled with a porous, filtering body, which has a very high value of effective internal surface. This surface serves as the working surface, at which a chosen component is being grouped, as a rule, through binding to a recognising reagent immobilised on this surface. The creation of a capillary or a porous structure in a probe volume provides for the increase of the surface, on which biochemical reactions occur, the quantity of magnetic particles being recorded and, consequently, the signal being measured.

To ensure selectivity of the analysis for the content of one or another analyte, the working surface is formed with immobilising a reagent on it, which is capable of binding (recognising) the analyte in a selective manner, and through this reagent said chosen component is being bound to the working surface.

To solve a number of practical problems, said probe volume is formed from several spatially separated regions, and the possibility to record said signal is ensured for each of said regions. First of all, such recording of information signal for each of several channels independently allows using the channels for generation of reference signals (i.e., reference channels) of various functions. For example, it is reasonable to exploit reference channels to compensate for probable occasional errors, scatter of parameters, inhomogeneities of samples of the mixture, as well as non-specific (non-selective) grouping of components of the mixture being analysed in the probe volume, and non-specific binding of the components to the working surface or to the magnetic particles. Besides, for repetitive analyses or continuous monitoring, reference channels can serve to take into account temperature drifts and other physical or chemical instabilities (e.g., pressure, density, pH of a solution or concentration of unwanted impurities in it, etc.). In such applications, as a rule, a reference channel is under the same conditions as an informative one, except for selective grouping of a chosen component (its binding to a recognising reagent).

Another group of tasks, in which multiple-channel recording is required, relates to providing for high throughput of analyses. This is of particular importance, for example, for testing new preparations in pharmaceutical industry. For solving such problems it is reasonable, in particular, to realise the proposed method on the basis of the current ELISA standards using sets of great number of reaction wells and, of course, with the use of magnetic labels instead of enzyme ones.

A third group of the tasks is the recognition of complex multi-component mixtures and their analysis for a number of components simultaneously. To do this, in said spatially separated regions a working surface is formed and on this working surface various reagents are immobilised, which are capable of binding various analytes selectively and through which chosen components are being bound to the working surface, and from recording said signal for each of several said regions the information on the contents of several analytes in the mixture being analysed is being obtained. In the simplest case, when the degree of selectivity of the binding of each chosen component with a respective recognising reagent is high enough, each of said regions is associated with no more than one such reagent and no more than one analyte; that is, one region is "responsible" for the recognition of one component, and some regions are used as reference channels. In other cases, from said regions a complex signal pattern is obtained, each signal has a low specificity to one or another component, but the entire pattern appears specific (as a fingerprint) to the mixture being analysed as a whole. In this case, the mixture can be identified, for example, with computer methods of pattern recognition. Such approaches are known with no connection to the proposed method and are referred to as "biochips", "gene chips", electronic "nose" and "tongue" etc.

The mentioned variants of the method, with forming the probe volume and, respectively, the working surface consisting in a number of spatially separated regions and providing for the recording of said signal for each of said regions independently, are realised, for example, by the interaction of the medium being analysed, or its parts, independently (in parallel) or successively with each of said regions. The variant of the parallel (not obligatory simultaneous) interaction is realised, for example, by the interaction of the mixture as a whole with a biochip, a gene chip, a chip for a combinatorial chemistry analysis, etc., or by dosing the portions of the mixture being analysed into titer plates containing arrays of reaction cells (ELISA-like, etc.). The variant of the successive interaction is realised, for example, by passing the mixture being analysed through a tube or a column so that the mixture passes the regions with different recognising reagents successively, and in each such region a corresponding chosen component is grouped.

One of preferable variants of said forming of the probe volume and, respectively, working surface from several spatially separated regions, with providing for recording said signal for each of said regions, consists in that each of these regions is provided with a separate magnetic induction meter, which is used to record said signal at a combinatorial frequency as described above. To do so, the output of each induction meter is connected with a radio-frequency filter, which is tuned to pass the combinatorial frequency signal, and a receiver of the output signal. In doing so, the probe volume is formed, for example, by making use of arrays of a large number of cells (wells), in each cell the grouping (selective binding) of a chosen component is ensured, and each cell is equipped with an independent magnetic induction meter. Standard titer plates, which are used in conventional biochemical analysis procedures, are preferably to employ as such arrays. A promising way is miniaturisation of such arrays. In particular, for recognition of complex mixtures and multi-component analyses, for example, relying on combinatorial chemistry methods, fabrication of the arrays of said regions as microelectronic chips is promising. In doing so, magnetic induction meters and circuitry components are preferable to make on the basis of planar microelectronic technology.

In other variants of the method, in which the probe volume and, respectively, the working surface are formed from a number of spatially separated regions and recording of said signal is enabled for each of said regions, this signal is recorded successively for said regions. In doing so, said probe volume consists of a number of spatially separated regions and is built so as to enable successive testing of said regions with a magnetic induction meter. For example, the probe volume is constructed so that said regions can be successively placed near the magnetic induction meter, or the magnetic induction meter near said regions. For example, a tube (column) is used, in which a probe volume is formed consisting of a number of regions, spatially separated along this tube (column). Therewith, in these regions different recognising reagents are immobilised which bind different chosen components selectively when the medium being analysed is passed through this column (tube). After this binding, the tube (column) is pulled in the immediate vicinity of the magnetic induction meter (e.g., pulled through an inductance coil), or the magnetic induction meter is moved along the tube (column). Beside such a tube, other formats can also be used. The examples are: a thick enough strip of a capillary-porous material, which strip is constructed and operates similarly to the tube, a two-dimensional array of said regions scanned with a magnetic induction meter, etc.

In order to ensure that the recording of the signal for each of said regions is independent of other regions, it makes sense to separate these regions with broad enough intermediate space. For example, in the above-described variant of the tube (column) inserted into the magnetic induction meter made as an inductance coil the distance between said regions along the tube should be of the same order as the coil diameter (no less than half the diameter, and preferably more than twice the diameter).

Furthermore, let us show that it is the distinctive features of the proposed method that provides the wanted technical result.

The grouping in a probe volume of a chosen component with magnetic particles attached to it provides for the enhancement of the method's sensitivity. Simultaneously, this lowers the cost of the method, improves the efficiency of the measurement operations, simplifies the apparatus, and lowers its weight and dimensions.

The same technical result is ensured by making said magnetic field alternating, pre-setting its spectrum with spectral components, at least, at two frequencies, and measuring said signal at a frequency, which is a linear combination of frequencies of said spectral components, during the exposure of said magnetic particles to said magnetic field. This all provides for stability and protection of the method against interference for a number of reasons. One of the reasons is avoiding dc measurements, which are always associated with the problem of drifts of a zero level, which is difficult to solve. Another reason is the absence of spectral components of acting signals in the spectrum of the signal extracted for the measurements, the orthogonality of the signals in a broad sense, which is the conventional criterion of high stability against interference. Short time duration of the measurements also favours the efficiency of the proposed method. Of even greater importance is the fact that recording of the signal during the exposure of the magnetic particles to the magnetic field enables one to avoid relying on the residual magnetisation of the particles, which is very low in the most practically important cases. As a consequence, the class or operable magnetic particles is substantially extended and the useful signal sharply increases. As this takes place, the technical result is realised, which consists in the enhancement of the signal-to-noise ratio resulting from the measurements, the increase of the accuracy of the measurements, the enhancement of the sensitivity of the method, and more reliability of the data obtained. At the same time, the costs of the experiment are lowered owing to the reduction of the number of necessary operation steps, time, amount and dimensions of necessary equipment. This enables the development of mobile, inexpensive, highly efficient mass test laboratories, and improves the operational flexibility of the method.

In preferable variants of the proposed method said linear combination of the frequencies of said spectral components is the sum or the difference of these frequencies. This ultimately narrows the used frequency spectrum, and, in turn, simplifies the embodiments of the method, reduces its costs, and improves the reliability.

Thus the proposed method allows achieving the wanted technical results in the simplest way and, hence, with minimal expenses.

It is also very important that the amplitude of, at least, one of said spectral components is chosen high enough to ensure a non-linear dependence of said magnetic induction on the strength of said magnetic field. The reason is that it is the non-linearity of the energy transformation of acting signals in the magnetic particle material that results in the appearance of a signal at a combinatorial frequency. In this case, the signal at the higher frequency should have preferably a lesser amplitude, because this signal plays the role of interference when the measured signal is distinguished on its background (in the temporal sense). This interference could considerably lower the sensitivity of the proposed method. Therefore the amplitudes $A_h$ and $A_l$ of said spectral components, which pertain to the higher and the lower frequencies, respectively, are chosen according to the relationship $A_l/A_h > 2$.

Besides, the magnetic strength vectors pertaining to, at least, two said spectral components are oriented in a number of cases non-collinear to each other. This is thought useful to raise the efficiency of the action of the external signal energy on the system of magnetic labels, for example, when recording spin echo signals. This provides the ac decoupling of the inductance coils and the absence of the influence of the magnetic field of one coil to the other one when the axis of one coil is turned by 90° with respect to the other. Besides, this enables one to optimise the conditions of non-linear interaction of the acting signals with the material of magnetic particles and hence to increase the level of the extracted signal. This increases the sensitivity of the method, which is the basis of all other above-mentioned characteristics of the wanted technical result.

The magnetic particles are made of a soft magnetic material to enhance the response of the particles to the acting magnetic field, because this response determines the value of the measured signal. This also provides the basis for the achievement of the wanted technical result.

The condition that in the probe volume a working surface is intentionally formed, and this surface meets the requirements for the recorded reaction of selective binding of a chosen component to occur, enhances the usable signal and, besides, increases the reliability of the results of the analysis. Further possibilities for the enhancement of the usable signal are opened through the use of a highly developed working surface with a high effective surface value or a three-dimensional binding matrix, since the probability and the number of elementary events of the mentioned binding increase with the increase of the effective surface accessible to the reaction.

One of the methods of the working surface formation consists in filling the probe volume with micro-granules. This provides for the increase of the surface accessible for the reaction to occur and hence the signal to be measured. In this case said granules are advisable to produce, for example, under low pressure from polyethylene stabilised with gamma-radiation. This provides for high stability of the working surface against destructive factors of chemical and mechanical nature. It should be noted that making use of polyethylene lowers the cost of the method as well. Besides, the accuracy and the reliability of the results are increased, since the chemical stability of polyethylene ensures the absence of undesirable side effects from the material on which the working surface is formed. Furthermore, one should take into account the ability of polyethylene produced under low pressure and stabilised with gamma-radiation to form micro-granules of size less than one micron. This ensures the formation of a high effective surface and, besides, increases the accuracy of the analysis method, its sensitivity and efficiency. Besides, the possibility for reducing the size of said spatially separated regions and, hence, of their denser arrangement is ensured. Similarly, filling the probe volume with a capillary-porous structure also enables one to increase the surface where biochemical reactions occur and, hence, the signal being measured.

All this makes the proposed method stable against external effects, such as mechanical (shaking, vibrating), thermal and chemical ones, since the presence of a solid carrier of the reaction products being analysed improves their isolation from the environment under the conditions of a transportable laboratory. The combined use of different formats of the reaction product carriers improves the reliability of the exploitation of the proposed method, ensures its operational flexibility, and extends its application area.

The immobilisation of a reagent, which is capable of selectively binding the analyte, on the working surface enables one to efficiently distinguish the information relevant just to the analyte from probable parasitic signals, increase the accuracy and the reliability of the results of the analysis.

The formation of the probe volume from a number of spatially separated regions with the possibility to record said signal for each of said regions independently enables a multi-parameter analysis of the mixtures under examination with a high degree of parallelisation. This allows lowering costs, when multi-parameter examinations are carried out, gives universality and operational flexibility to the proposed method, simplifies its apparatus embodiment, reduces dimensions and weight, opens opportunities for the development of mobile stations and laboratories for mass tests of probes and investigations of population.

Besides, the formation of the probe volume from a number of spatially separated regions with the possibility of their independent and parallel monitoring substantially increases the throughput of the proposed method, lowers the cost per one analysis, improves the reliability of the results obtained, taking into account the increase in the amount of statistical data.

The condition that in said regions a working surface is formed with immobilising on the surface various reagents, which are capable of binding various analytes selectively and through which chosen components are being bound to the working surface, and from recording said signal for each of several said regions the information on the contents of several analytes in the mixture being analysed is being obtained, provides for the same technical result applying to the analysis of complex mixtures for the contents of a number of components simultaneously and to the recognition of such mixtures.

As a realisation of the method discussed above, an apparatus is proposed to read information in the method of analysis of a mixture of biological and/or chemical components. This apparatus refers to the field of development and improvement of apparatus for registration of the results of biochemical analyses. The drawbacks of the analogue-apparatus are eliminated in the proposed apparatus for analysis of a mixture of biological and/or chemical components, which comprises:

a chosen component of the mixture being analysed, said component being spatially arranged in a prescribed manner;

magnetic particles attached to the chosen component of the mixture being analysed, directly or through an intermediate material;

a magnetic field generator, within which action said magnetic particles are situated;

a meter of the magnetic induction produced by said magnetic particles;

an output signal receiver;

a block generating the result, which input is connected to the output of the output signal receiver, which elements coincide with essential features of the analogue-apparatus.

The difference from the prototype consists in that:

the chosen component of the mixture being analysed with magnetic particles attached to this component is grouped in a probe volume;

the magnetic field generator is made so as to allow pre-setting the frequency spectrum of the magnetic field with spectral components, at least, at two frequencies;

a radio-frequency filter is included, which input is connected to the output of the magnetic induction meter, and the output of the filter is connected to the output signal receiver, the filter being tuned to pass the signal at a picked-out frequency, which is a linear combination of the frequencies of said spectral components.

Besides, said linear combination of the frequencies of said spectral components is the sum or the difference of these frequencies.

Besides, the magnetic field generator comprises an alternating current (ac) generator made so as to allow pre-setting the frequency spectrum of its output signal with spectral components, at least, at two frequencies, and an inductive block connected to the output of said ac generator, the output of the inductive block being the output of the magnetic field generator.

Besides, said inductive block serves as said magnetic induction meter.

Besides, said inductive block is made as an inductance coil with no core, the first lead of the coil being connected to the output of said ac generator and the second lead being connected to chassis.

Besides, said inductive block comprises two inductance coils without cores, the first leads of said coils being connected, respectively, to the first and the second output of said ac generator, the second leads of the coils being connected to chassis, and, besides, the first lead of one of said coils being connected to the input of said radio-frequency filter.

Besides, the axes of said coils are tilted with respect to each other.

Besides, the angle between the axes of said coils is 90°.

Besides, a phase regulator is inserted between one of the outputs of said ac generator and the associated first lead of one of said coils, said phase regulator being provided with a control input for entering the data on the angle that the axis of this coil makes with the axis of the other coil.

Besides, the magnetic induction meter comprises an inductive element with no core, said element being not a part of said magnetic field generator.

Besides, the magnetic induction meter comprises a magnetoresistive (magneto-impedance) sensitive element.

Besides, the magnetic induction meter comprises a sensitive element based on the Hall effect.

Besides, the magnetic induction meter is made as a planar microelectronic structure.

Besides, the radio-frequency filter has the property to reject the signal of that of the frequencies of said spectral components, which is the nearest to said picked-out frequency.

Besides, the radio-frequency filter has the property to reject the signal of that of the frequencies of said spectral components, which is the nearest to said picked-out frequency, and, besides, the radio-frequency filter is controllable, the control input of the radio-frequency filter being connected to the control output of said ac generator.

Besides, a reference signal generator is inserted, which is connected through its input to the output of said ac generator, through the second, control, input to the output of the output signal receiver, and through its output to the second input of said radio-frequency filter, said filter being made lock-in.

Besides, a control block is inserted, which first and second outputs are connected to the control inputs of said ac generator and said radio-frequency filter, respectively, and the input is connected to the control output of the output signal receiver.

Besides, the reference signal generator and the output signal receiver are made as a processor.

Besides, the output signal generator, the output signal receiver, and said ac generator are made as a processor.

Besides, the magnetic particles are made of a soft magnetic material.

Besides, in said probe volume a working surface is formed, to which the chosen component of the mixture being analysed is bound, said magnetic particles being attached to this component.

Besides, the working surface is formed in the probe volume filled with micro-granules.

Besides, said micro-granules are made of polyethylene.

Besides, said micro-granules are produced under low pressure from polyethylene stabilised with gamma-radiation.

Besides, the working surface is formed in the probe volume filled with a capillary-porous structure.

Besides, on the working surface a reagent is immobilised, which is capable of selectively binding the analyte, the chosen component of the mixture being analysed being bound to said reagent, and, through this reagent, to the working surface.

Besides, said probe volume consists of several spatially separated regions, each of these regions being provided with a separate magnetic induction meter, which output is connected to a radio-frequency filter and an output signal receiver.

Besides, said probe volume consists of several spatially separated regions and is made so as to enable successive testing of said regions with a magnetic induction meter.

Besides, the ac generator and the output signal receiver are made as a processor.

Figure 1:
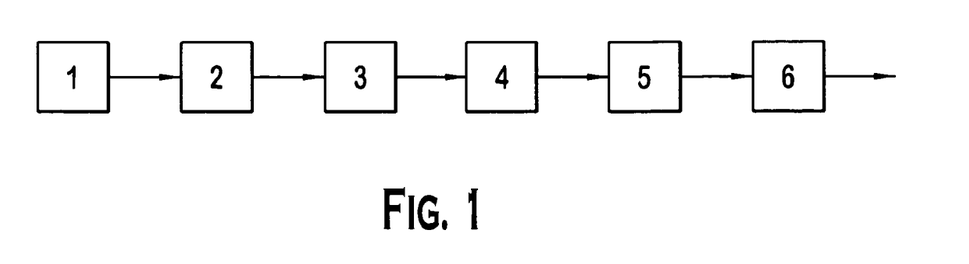
FIG. 1 is a block diagram of an apparatus in accordance with the invention.

In FIG. 1 the basic variant of a proposed apparatus according to the invention is schematically shown.

Figure 2:
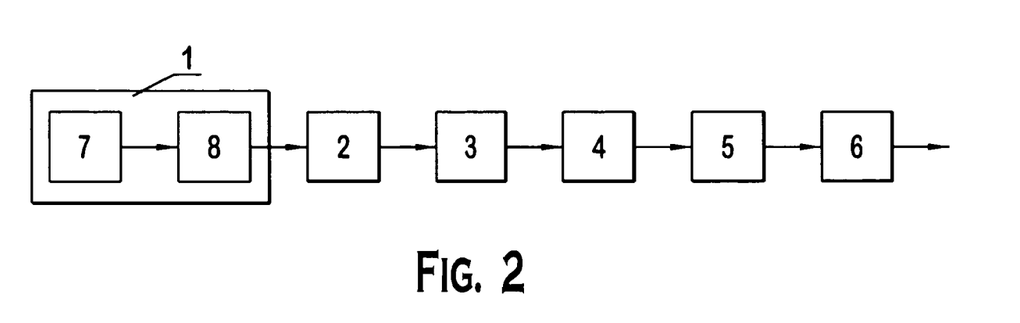
FIG. 2 is a block diagram of another apparatus in accordance with the invention.

In FIG. 2 the variant of a proposed apparatus according to the invention is schematically shown, with the magnetic field generator made from an ac generator and an inductive block connected in series.

Figure 3:
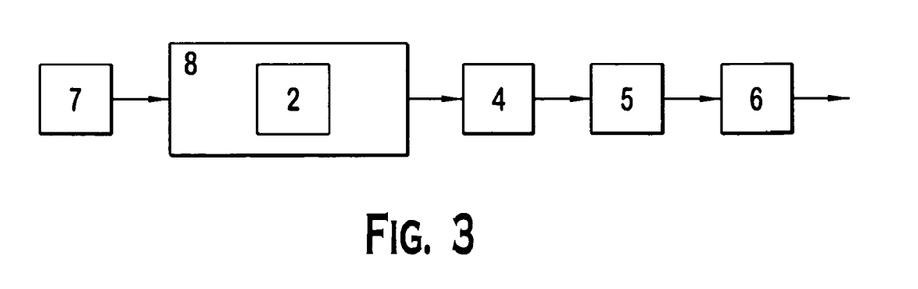
FIG. 3 is a block diagram of another apparatus in accordance with the invention.

In FIG. 3 the variant of a proposed apparatus according to the invention is schematically shown, with the inductive block functioning as the magnetic induction meter.

Figure 4:
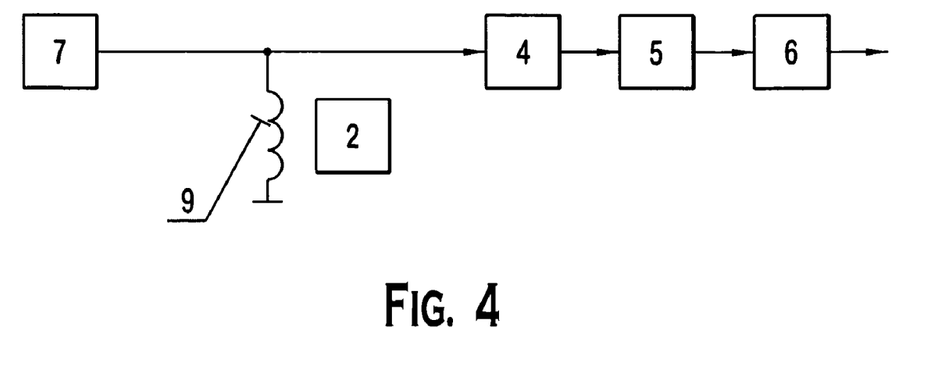
FIG. 4 is a block diagram of another apparatus in accordance with the invention.

In FIG. 4 the variant of a proposed apparatus according to the invention is schematically shown, with the inductive block made as an inductance coil.

Figure 5:
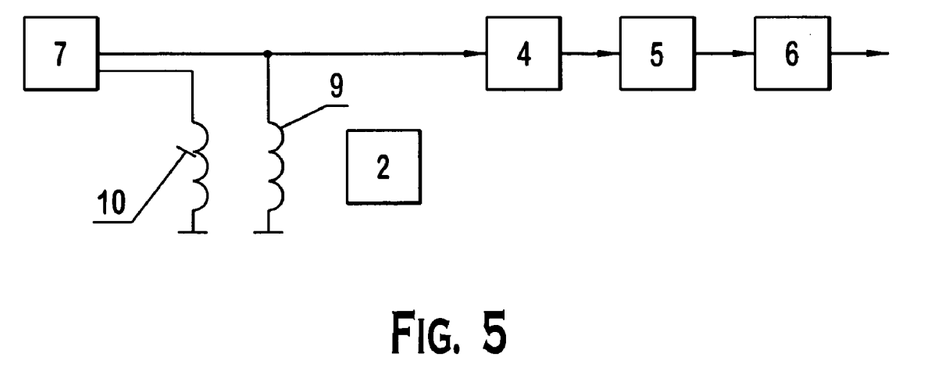
FIG. 5 is a block diagram of another apparatus in accordance with the invention.

In FIG. 5 the variant of a proposed apparatus according to the invention is schematically shown, with the inductive block made as two inductance coils.

Figure 6:
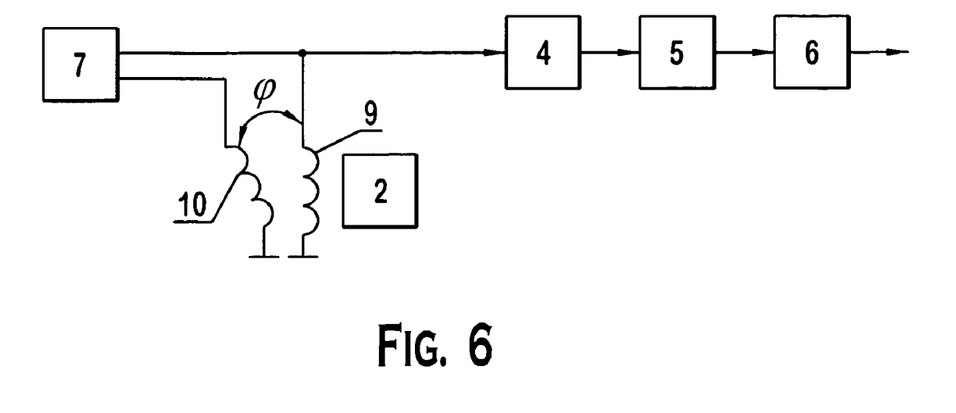
FIG. 6 is a block diagram of another apparatus in accordance with the invention.

In FIG. 6 the variant of a proposed apparatus according to the invention is schematically shown, with the inductive block made as two inductance coils tilted at a certain angle with respect to each other.

Figure 7:
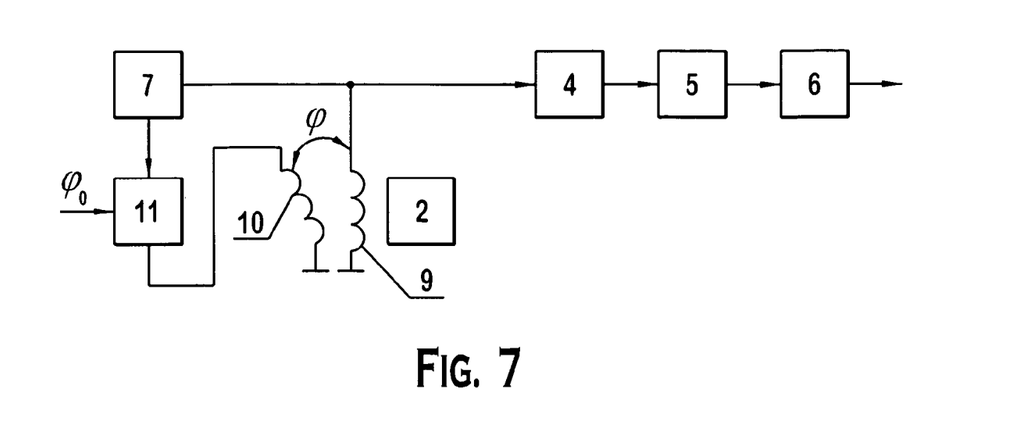
FIG. 7 is a block diagram of another apparatus in accordance with the invention.

In FIG. 7 the variant of a proposed apparatus according to the invention is schematically shown, with the inductive block made as two inductance coils tilted at a certain angle with respect to each other, and with a phase regulator in the circuit of one of the coils.

Figure 8:
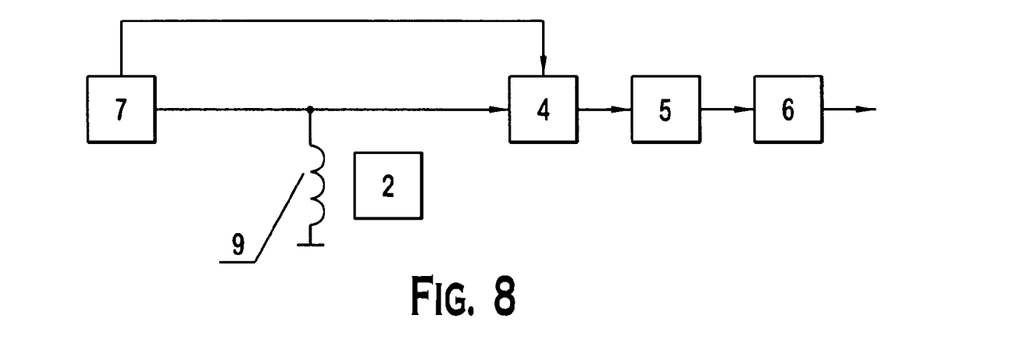
FIG. 8 is a block diagram of another apparatus in accordance with the invention.

In FIG. 8 the variant of a proposed apparatus according to the invention is schematically shown, with the inductive block made as an inductance coil and with a rejecting filter in the signal receiving circuit.

Figure 9:
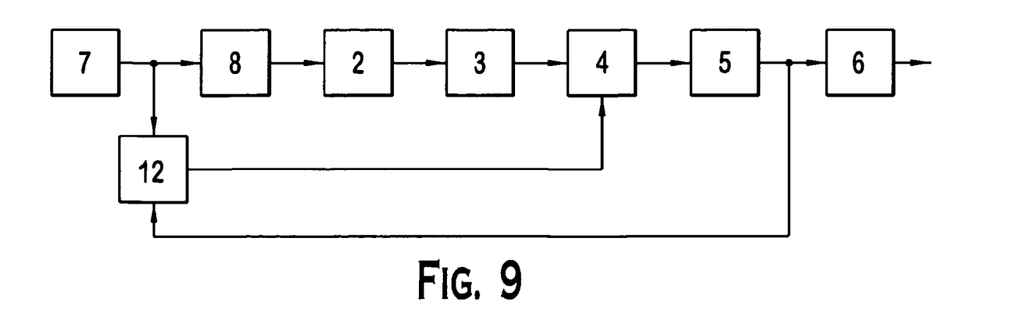
FIG. 9 is a block diagram of another apparatus in accordance with the invention.

In FIG. 9 the variant of a proposed apparatus-according to the invention is schematically shown, where the filter is lock-in.

Figure 10:
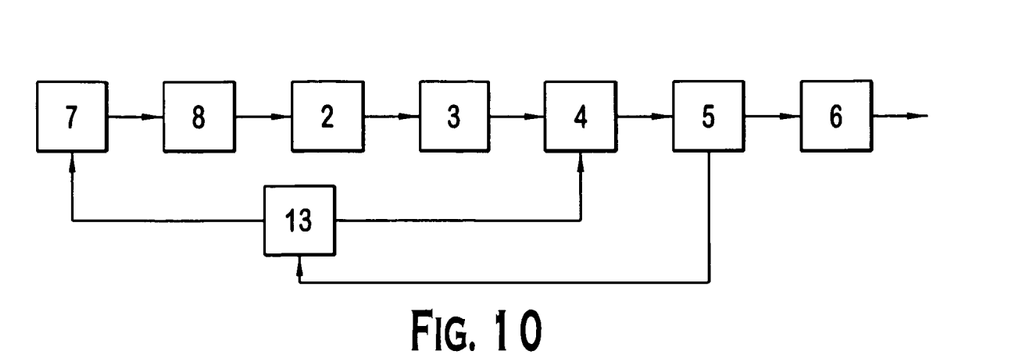
FIG. 10 is a block diagram of another apparatus in accordance with the invention.

In FIG. 10 the variant of a proposed apparatus according to the invention is schematically shown, where connections of a control block are depicted provided that this block is included in the apparatus.

Figure 11:
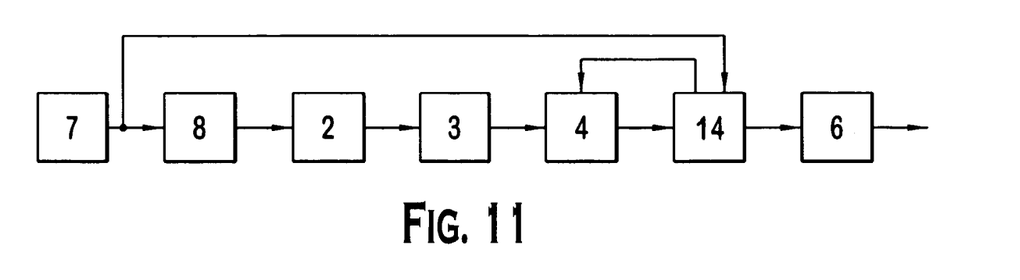
FIG. 11 is a block diagram of another apparatus in accordance with the invention.

In FIG. 11 the variant of a proposed apparatus according to the invention is schematically shown, with a processor combining the functions of a reference signal generator and the output signal receiver.

Figure 12:
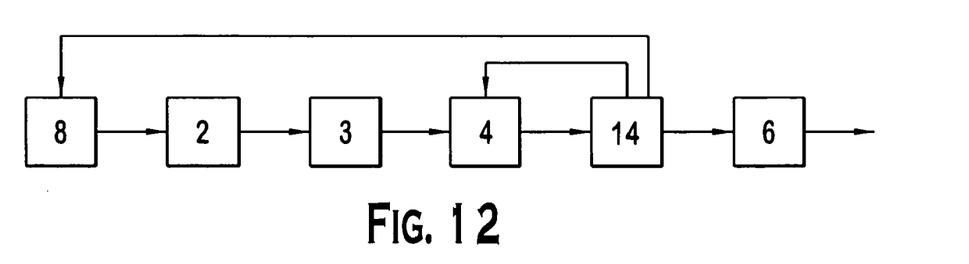
FIG. 12 is a block diagram of another apparatus in accordance with the invention.

In FIG. 12 the variant of a proposed apparatus according to the invention is schematically shown, with a processor combining the functions of the ac generator, the output signal receiver, and the reference signal generator.

Figure 13:
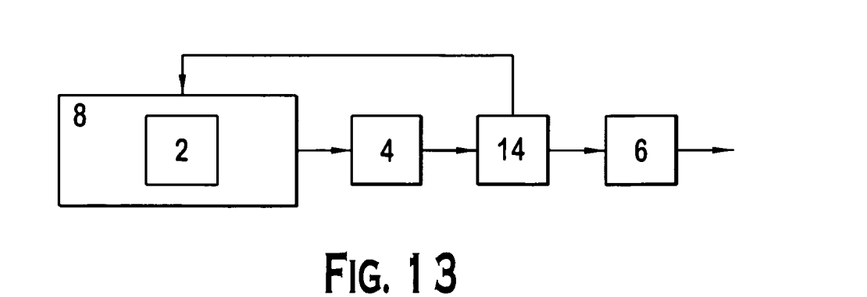
FIG. 13 is a block diagram of another apparatus in accordance with the invention.

In FIG. 13 the variant of a proposed apparatus according to the invention is schematically shown, with a processor combining the functions of the ac generator and the output signal receiver.

In FIGS. 1 to 13 the following notations are used:

1, magnetic field generator; 2, the total of magnetic particles attached to a chosen component of the mixture being analysed and grouped in a probe volume; 3, magnetic induction meter; 4, radio-frequency filter; 5, output signal receiver; 6, block generating the result; 7, ac generator; 8, inductive block; 9, first inductance coil; 10, second inductance coil; 11, phase regulator; 12, reference signal generator, 13, control block; 14, processor.

MODES OF CARRYING OUT THE INVENTION

The proposed method can be realised by apparatus for analysis of a mixture of biological and/or chemical components.

The proposed apparatus operates as follows. The generator 1 acts with an alternating magnetic field on the magnetic particles 2 (FIG. 1). For example (FIG. 4) the generator 1 produces the alternating magnetic field inside the coil 9. The magnetic field has, at least, two spectral (frequency) components, for example, with the frequencies $f_1=100$ kHz and $f_2=100$ Hz. The response of the magnetic particles to their exposure to the magnetic field is their magnetisation or magnetic induction. One exploits the particles, which possess magnetic properties to one extent or another, in particular, non-linear dependences of the magnetisation and the magnetic induction on the strength of an external magnetic field. Owing to this a spectral re-distribution of the excitation energy occurs, and combinatorial spectral components arise in the spectrum of the magnetic particles response to the action of the field. In general, these components are linear combinations of frequencies $f_1$ and $f_2$ of the form $f_i=mf_1+nf_2$, where m, n are positive or negative integers other than zero. In principle, such a linear combination may also be contributed to by more spectral components. The values of m and n can vary, as the case requires. For example, said linear combination may have the form $f_i = f_1 \pm f_2$ (the sum and the difference frequencies), $f_i = f_1 \pm 2 f_2$, and so on. It is known that the intensity of spectral components decreases with the harmonic number. Therefore, to obtain the maximum signal amplitude, the values m=1 and n=±1 are preferable to use. This corresponds to the sum or the difference of the frequencies of spectral components of the acting magnetic field.

Let us remind that prior to the measurements the chosen component and the magnetic particles attached to it are spatially arranged in a prescribed manner and grouped in the probe volume, for example, through the reaction of selective binding of the chosen component by a complementary recognising reagent. The chosen component is considered to be either the analyte itself or another component (e.g., which competes with the analyte for binding to the recognising reagent), intrinsic to the mixture being analysed or intentionally introduced into this mixture the quantitative measure of the grouping of said chosen component in the probe volume indicating the content of the analyte in the mixture being analysed.

The magnitude of the recorded magnetic induction signal at a combinatorial frequency is unambiguously determined by the amount of the magnetic particles 2 grouped in the probe volume. Consequently, on extracting the signal at a combinatorial frequency with the filter 4, one obtains the information on the amount of the magnetic labels 2 in the probe volume from the output of the receiver 5. To do this, the receiver 5 is made in accordance with any known scheme, which are used in the methods of noise-immune receiving of low-intensity signals against a noise and interference background. The receiver 5 fulfils also the functions of amplification, detection, and accumulation.

The eventual result, i.e., quantitative data on the content of the analyte, is formed by the block 6 for generating the result. The parameters of the block 6 take into account specific features of the sample of the mixture being analysed and the operations performed with it.

In a preferable variant of the apparatus the magnetic field generator 1 consists in an ac generator 7, which is made so as to allow pre-setting the frequency spectrum of its output signal with spectral components, at least, at two frequencies, and an inductive block 8 connected to the output of said ac generator 7 (FIG. 2). This enables the required action on the sample being tested. As discussed earlier for the proposed method, the pre-setting of the frequency spectrum is advisable to take into account spectral features of the interaction of the generated high-frequency magnetic field with the sample being measured.

As this takes place, one can significantly simplify the apparatus, if said inductive block 8 of the magnetic field generator serves simultaneously as the magnetic induction meter 3 (FIG. 3). This is reasonable in magnetic measurements, in which a common coil often operates simultaneously as an exciting coil and as a receiving one. This variant is preferable for one-channel apparatus. However, these functions are advisable to separate for multi-channel apparatus, in which the probe volume consists of a number of spatially separated regions. For example, the block 8 generates a magnetic field common for all said regions, and each region is provided with an individual magnetic induction meter. Another case of separating these functions is making the meter 3 on the basis of not inductive, but another magneto-sensitive element (see below).

In the simplest variant, said inductive block 8, which also serves as the magnetic induction meter, is made as an inductance coil 9 with no core, the first lead of this coil being connected to the output of said ac generator 7, and the second lead being connected to chassis (FIG. 4).

In another variant of the proposed apparatus (FIG. 5), in the inductive block a second inductance coil 10 is included, which is connected through its first lead to the second output of the generator 1, and through the second lead to chassis. In this case one of the spectral components of the output signal comes from the first output of the generator 1 to the coil 9, and the other spectral component does from the second output of the generator 1 to the coil 10.

In another variant of the proposed apparatus according to (FIG. 6) the axes of said coils 9 and 10 are tilted with respect to each other. As a result, the magnetic field strength vectors of two said spectral components make some angle in the sample 2. Due to variation of this angle in the sample under test it is possible to raise the efficiency of the non-linear transformation of partial components of the magnetic field into the magnetic induction signal to be recorded, and hence to increase signal-to-noise ratio.

As this takes place, the angle between the axes of said coils is 90° in one of realised variants of the apparatus.

In another variant of the proposed apparatus (FIG. 7) a phase regulator 11 is included, which is inserted between one of the outputs of said generator 1 and the associated inductance coil 9 or 10, said phase regulator being equipped with a control input for entering the data $\phi_0$ on the angle that the axis of this coil makes with the axis of the other coil. This opens additional opportunities to control the phase of one of spectral components of the exciting signal.

If, for some reasons, it is advisable to separate the magnetic induction meter 3 and the magnetic field generator 1, one may realise the meter 3 using a number of alternative methods of magnetic induction measurements. For example, in the scheme of FIG. 1 the magnetic induction meter comprises an inductive element with no core, or a magnetoresistive (magneto-impedance) sensitive element, or a sensitive element based on the Hall effect. As this takes place, in a preferable variant of the apparatus the magnetic induction meter is made as a planar microelectronic structure.

In another variant of the proposed apparatus, which can be illustrated by any of the schemes of FIG. 1 to 7 and others, except for the variants in which the filter 4 is lock-in, the filter 4 is a rejecting filter, which has the property to suppress that spectral component of the acting signal, which is the nearest to said picked-out frequency. Then, if the Q-factor of said filter 4 is high enough, even powerful interference at the frequency neighbour to the picked-out one can be suppressed down to a sufficiently low level without noticeable attenuation of the usable signal.

It should be noted that the higher of the two frequencies of the acting signal spectrum is usually rejected. The combinatorial frequency lies, of course, near the higher frequency, which signal, if no rejection, could come to the receiver 5 and substantially degrade signal-to-noise ratio.

In another variant of the proposed apparatus (the scheme of FIG. 8) the filter 4 is made controllable, and its control input is connected to the control output of the generator 7, the frequency of which signal is the nearest to said picked-out frequency. The introduced connection of the mentioned output of the generator 7 to the control input of the filter 4 enables one to tune the frequency rejected by the filter 4, thus compensating for instabilities of said generator 7.

In this case one should note that the characteristics of interference suppression by filters usually correlate with the absolute value of the frequency shift of a picked-out frequency relative to the transmission band of the filter 4. It is known that the frequency drift of a generator signal is usually proportional to its nominal frequency. Therefore, in the proposed apparatus one expects the drift of the high-frequency spectral component of the generator 7 to be 3 orders higher than that of the low-frequency component. That is why the filter 4 is tuned by the signal of the higher frequency of the acting signal spectrum. It is this frequency that is the closest to the picked-out combinatorial frequency.

In the proposed apparatus according to (the scheme of FIG. 9) the reference signal generator 12 receives at its input the exciting signal from the output of the generator 1, which has, for example, two spectral components. Then, the reference signal generator 12 yields at its output a harmonic signal at a combinatorial frequency, this signal being used as a reference (locking) signal for the lock-in filter 4. The latter is a multiplier. It picks out the corresponding combinatorial component from the mixed signal and noise in the optimal manner, according to the Kotel'nikov's theory. Account is taken of further accumulating of the multiplication result in the output signal receiver 5, and making the multiplied components in phase through tuning the reference signal generator 12, which control input receives the feedback signal from the output of the output signal receiver 5.

In another variant of the proposed apparatus (FIG. 10), a control block 13 is inserted, which first and second outputs are connected to the control inputs of said generator 7 and said radio-frequency filter 4, respectively, and the input is connected to the control output of the output signal receiver 5. By analysing a change in the output signal due to changes in the parameters of the generator 7 and the filter 4, the control block 13 generates the optimal controlling action on said blocks 7 and 4 through feedback loops.

In another variant of the proposed apparatus (FIG. 11) a processor 14 combines the functions of said reference signal generator 12 and said receiver 5. This is advisable from the viewpoint of using modern technology capabilities, and for the compatibility of the proposed apparatus with modern component types.

In another variant of the proposed apparatus (FIG. 12) a processor 14 combines the functions of said reference signal generator 12, receiver 5, and ac generator 7. This is advisable for the same reasons.

In another variant of the proposed apparatus (FIG. 13) a processor 14 combines the functions of said ac generator 7 and output signal receiver 5. This is advisable for the same reasons.

It should be pointed out that in addition to the above-mentioned variants of combinations of block functions in one processor various combinations of these variants are possible as well, including those in which the processor fulfils simultaneously the functions of the control block 13.

Furthermore, let us show that it is distinctive features of the proposed apparatus that ensures the wanted technical result.

The grouping of a chosen component of the mixture being analysed, with magnetic particles attached to it, in a probe volume provides for the increase in the apparatus sensitivity and the improvement of parameters of its output signal. This is due to the increase of the number of particles, magnetic induction carriers, in the confined probe volume, where the measurements are carried out, in close proximity to the magnetic induction meter. The latter can be miniature and, in a number of cases, realised on the basis of the planar microelectronics technology. All these features allow lowering the cost of the apparatus, simplifying its embodiment, and decreasing weight and dimensions as well. Besides, the efficiency of the measurements is improved, since the realisation of the characteristics needed without pre-concentrating magnetic particles would require the use of data accumulation methods associated with extra time and device needs.

The realisation of the magnetic field generator with the capability of pre-setting the frequency spectrum of the magnetic field with spectral components, at least, at two frequencies, and the insertion of a radio-frequency filter between the output of the magnetic induction meter and the input of the output signal receiver, said filter being tuned to pass the signal of the picked-out frequency, which is a linear combination of the frequencies of said spectral components, enables one to drastically enhance the usable signal against noise and to improve the stability and the immunity to interference for a, number of reasons. Among these reasons, first, is going away from relying on the residual magnetisation of particles, which is very low for small particles. Second, it is avoiding dc measurements, which are always associated with the problem of zero drifts, which is difficult to solve. Third, these are the absence of spectral components of acting signals in the spectrum of the signal picked-out for measurements and the orthogonality of these signals in broad sense. The latter condition is the conventional criterion of high immunity to interference and enables one to efficiently distinguish the information signal from the external magnetic field, fluctuation noise, and apparatus interference.

In doing so, the technical result is achieved, which consists in the increase of the signal-to-noise ratio resulted from the measurements, increase in the measurement accuracy, enhancement of the apparatus sensitivity, improvement of the reliability of the data obtained, with simultaneous lowering of experimental costs owing to the reduction of the number of operations needed, time, amount and dimensions of apparatus needed, in the opportunities for the development of mobile, inexpensive, high-throughput mass test laboratories, and, hence, in higher operational flexibility of the proposed apparatus.

The feature that the picked-out frequency is the sum or the difference of the frequencies of said spectral components of the acting magnetic field narrows the used frequency band ultimately, provides for maximising the amplitude of the generated usable signal owing to minimising the number of a picked-out harmonics. This also improves stability and immunity to interference, simplifies the device embodiment, lowers cost, and improves reliability. Thus, the proposed apparatus provides for achieving the above-mentioned wanted technical results in the simplest way and with minimal expenses.

One should note that, in general, an alternating magnetic field generator could be realised in different ways, for example, with a rotating magnet or with an ac generator. In the latter case, as shown in FIG. 2, the magnetic field generator comprises an ac generator made so as to allow pre-setting the frequency spectrum of the output signal with spectral components, at least, at two frequencies, and an inductive block connected to the output of said ac generator. This technical solution provides for the reduction of the apparatus dimensions due to the use of modern microelectronic technologies. In doing so, the functions of a number of electronic blocks are eventually combined in a processor (block 14 in FIGS. 11 to 13), ensuring the above-mentioned wanted technical result.

Besides, the feature that said inductive block of the magnetic field generator fulfils the functions of the magnetic induction meter, ensures the compactness of the realised technical solution, improves the reliability of the apparatus, lowers its cost, thus providing the basis for the realisation of the above-mentioned technical result.

This is also favoured by making said inductive block as an inductance coil with no core, the first lead of the coil being connected with the output of said ac generator, and the second lead being connected to chassis. Actually, the absence of the core lowers internal noise of the apparatus, eliminates the noise intrinsic to a core, which is due to the inhomogeneity of magnetisation processes in magnetic materials, and lowers the weight and the dimensions of the apparatus. This also opens the possibilities for the miniaturisation of the apparatus and the employment of modern microelectronic technologies. The mentioned factors provide for further lowering of the measurement threshold, enhancing sensitivity, and improving stability and immunity to interference of the apparatus.

The feature that said inductive block comprises two inductance coils with no cores, first leads of said coils being connected to, respectively, the first and the second outputs of said ac generator, second leads being connected to chassis, and, besides, the first lead of one of the coils being connected to the input of said filter, enables one to realise the filter 4 of higher orders and higher Q-factors, taking into account parasitic capacitances and inductances usually existing in schemes. Consequently, the apparatus possesses higher stability against interference and hence the above-mentioned wanted technical result is ensured.

The feature that the axes of said coils are tilted with respect to each other results in that the magnetic fields of the two spectral components are crossed at some angle in the sample. In this case, variation of the crossing angle in the sample under test provides for extra possibilities to gain the efficiency of non-linear interaction of the spectral components of the exciting signal with magnetic particles 2 of the sample under test. This favours for further lowering of the measurement threshold, increase of sensitivity, immunity and stability to interference of the apparatus.

The feature that the rotation angle of the axis of the second coil relative to the first one is 90° ensures the conditions needed to the use of alternative methods for information signal formation, e.g., using spin precession.

This is also favoured by that the phase regulator 11 is inserted between the second output of the alternating current generator 7 and the first lead of the second inductance coil, the data $\phi_0$ on the rotation of the second coil axis relative to the first one entering the control input of the phase regulator. The mentioned features also lead to the wanted technical result.

The presence of the inductance coil with no core in the magnetic induction meter 3 has the same advantages as the presence of a similar coil in the inductive block 8. This solution is preferable for the apparatus discussed, which measures very small quantities, because of both the high apparatus sensitivity needed and a low signal amplitude at the picked-out frequency, which results from a combinatorial interaction under the condition of magnetic non-linearity of the material of magnetic particles.

Besides, to tackle the problems in broad ranges of external parameters and to ensure the functional flexibility of the apparatus, the magnetic induction meter contains either a magnetoresistive (magneto-impedance) sensitive element or a sensitive element based on the Hall effect. Furthermore, it is advisable to make said magnetic induction meter as a planar microelectronic structure. Then it could be realised on the basis of industrial microelectronic technologies and mass production, thus providing for lowering of costs, weight, and dimensions of the apparatus, and improvement of its reliability.

The wanted technical result is favoured also by that the radio-frequency filter has the property to reject that harmonic component of the exciting signal, which has the frequency nearest to the picked-out combinatorial frequency. The reason is that the most dangerous interference is eliminated, which otherwise could influence the sensitive cascades of the receiver by bringing non-linear components into the received signal spectrum, lower signal-to-noise ratio and reliability of the results obtained.

Further improvement of the quality of the information receiving with simultaneous reduction in the requirements to the device quality is ensured by that the radio-frequency filter 4 is made controllable, its control input being connected to the control output of the generator 7. In this case the requirements for the stability of the generator 1 can be substantially reduced, since the drift of the exciting signal frequency is compensated for by proper tuning of the filter 4 characteristics.

The feature that the reference signal generator 12 is introduced, which has the input connected to the output of said ac generator 7, the second, control, input, connected to the output of the output signal receiver 5, and the output connected to the second input of said radio-frequency filter 4, which is made lock-in, ensures further gain in the efficiency of distinguishing weak information signals from noises. This enables one to realise optimal conditions for signal receiving and to achieve the wanted technical result.

Further opportunities to improve the apparatus arise from that the control block 13 is introduced, which first and second outputs are connected with control inputs of said ac generator 7 and radio-frequency filter 4, respectively, and the input of the block 13 is connected to the control output of the output signal receiver 5. In this case the control block 13, which functions can be fulfilled by a microprocessor or a computer, analyses the change of the output signal with changes of parameters of the generator 7 and the filter 4, and, as a result, generates, the optimal controlling action on said blocks 7 and 4 through feedback loops. In doing so, ultimate characteristics of the apparatus are realised, the operational flexibility is improved and the application area is extended.

Further opportunities to improve the apparatus stem from that the fulfillment of the functions of various combinations of blocks in the proposed apparatus, except for the inductive block 8, block 6 forming the result, and the filter 4, is ensured through the introduction of the processor 14, e.g., made as a microprocessor or a computer. In doing so, ultimate characteristics of the apparatus are realised, operational flexibility is improved, and the application area is extended. Besides, this opens the possibility to develop mobile, inexpensive, high-throughput laboratories for mass tests.

Thus, it is shown that the wanted technical result is actually achieved owing to the distinctive features of the proposed apparatus. The experiments done have demonstrated the feasibility of the proposed method and apparatus.

INDUSTRIAL APPLICABILITY

The proposed method and apparatus can be used for biological and chemical analyses, and also for development of chemical and biological sensors.

The invention claimed is:
1. A method of analysis of an analyte in a mixture of biological and/or chemical components, comprising:
choosing a component for attaching magnetic particles thereto or a component that is already attached to magnetic particles, wherein such component defines a cho- sen component, the chosen component allows generating quantitative data on the content of the analyte in the mixture being analysed, introducing the analyte and the chosen component within a probe volume comprising a recognizing reagent capable of binding the analyte and the chosen component in a selective manner and thereby spatially arranging the chosen component therein, attaching magnetic particles either directly or indirectly to the chosen component, either before or after the step of introducing the analyte and the chosen component within the probe volume, or using the chosen component that is already attached to magnetic particles, exposing the magnetic particles attached to the chosen component within the probe volume to a magnetic field, recording a signal due to the magnetic induction produced by the magnetic particles as a result of their exposure to the magnetic field, generating quantitative data on the content of the analyte in the mixture being analysed from the value of the signal, wherein the magnetic field has a spectrum, and the spectrum is pre-set with spectral components at least at two frequencies, wherein the amplitude of at least one of the spectral components is chosen high enough to ensure a non-linear dependence of the magnetic induction on the strength of the magnetic field; and the signal is recorded at such a frequency that is a linear combination of the frequencies of the spectral components during the exposure of the magnetic particles to the magnetic field.

2. A method as defined in claim 1, wherein the linear combination of the frequencies of the spectral components is the sum or the difference of these frequencies.

3. A method as defined in claim 1, wherein the magnetic particles are made of a soft magnetic material.

4. A method as defined in claim 1, wherein the probe volume comprises a working surface, and the chosen component is spatially arranged through binding this component to the working surface.

5. A method as defined in claim 4, wherein the working surface comprises micro-granules.

6. A method as defined in claim 4, wherein the working surface comprises the recognizing reagent, and the chosen component is bound to the working surface via the recognizing reagent.

7. A method as defined in claim 1, wherein the probe volume comprises a plurality of spatially separated regions, and the possibility to record the signal is ensured for each of the regions.

8. A method as defined in claim 1, wherein the probe volume comprises a plurality of spatially separated regions, each region comprising an independent working surface, each working surface comprising a recognizing reagent capable of binding a respective analyte and a respective chosen component in a selective manner and through which the respective chosen component is bound to the working surface of the respective region, and by recording the signal for each region the information on the contents of different analytes in the mixture is obtained.

9. A method as defined in claim 1, wherein introducing the analyte and the chosen component within the probe volume is preformed by one of the following processes: by sedimentation, by exposure to an inhomogeneous magnetic field or by filtration.

10. A method as defined in claim 1, wherein the magnetic particles are superparamagnetic.

11. A method as defined in claim 1, wherein magnetic field strength vectors pertaining to the at least two spectral components are oriented non-collinear to each other.

* * * * *